(12) United States Patent
McCauley

(10) Patent No.: US 8,549,893 B2
(45) Date of Patent: Oct. 8, 2013

(54) SYSTEM AND METHOD FOR A GAS CHROMATOGRAPH TO MASS SPECTROMETER INTERFACE

(75) Inventor: Edward B. McCauley, Cedar Park, TX (US)

(73) Assignee: Thermo Finnigan LLC, San Jose, CA (US)

( * ) Notice: Subject to any disclaimer, the term of this patent is extended or adjusted under 35 U.S.C. 154(b) by 743 days.

(21) Appl. No.: 12/399,574

(22) Filed: Mar. 6, 2009

(65) Prior Publication Data

US 2010/0223978 A1 Sep. 9, 2010

(51) Int. Cl.
*G01N 30/02* (2006.01)

(52) U.S. Cl.
USPC .......................................................... 73/23.37

(58) Field of Classification Search
USPC .......................................................... 73/23.37
See application file for complete search history.

(56) References Cited

U.S. PATENT DOCUMENTS

| | | | |
|---|---|---|---|
| 4,594,506 A | 6/1986 | Ghaderi | |
| 4,641,541 A | 2/1987 | Sharp | |
| 4,804,839 A | 2/1989 | Broadbent et al. | |
| 4,985,625 A | 1/1991 | Hurst | |
| 5,028,243 A | 7/1991 | Rubey | |
| 5,083,450 A * | 1/1992 | Grindstaff | 73/23.25 |
| 5,281,397 A | 1/1994 | Ligon et al. | |
| 5,686,655 A | 11/1997 | Itoi | |
| 5,837,883 A * | 11/1998 | Itoi | 73/23.37 |
| 6,006,584 A | 12/1999 | Itoi | |
| 6,126,728 A | 10/2000 | Walsh et al. | |
| 6,907,768 B2 | 6/2005 | Gass et al. | |
| 7,385,191 B1 * | 6/2008 | McMurtry et al. | 250/288 |
| 2003/0003595 A1 * | 1/2003 | Amirav | 436/173 |
| 2005/0211098 A1 | 9/2005 | Shimomura | |
| 2006/0011829 A1 | 1/2006 | Scheidemann et al. | |
| 2007/0104471 A1 | 5/2007 | Hannigan et al. | |
| 2008/0048107 A1 * | 2/2008 | Mcewen | 250/282 |
| 2008/0083874 A1 | 4/2008 | Prest et al. | |
| 2008/0142701 A1 | 6/2008 | Prest | |

OTHER PUBLICATIONS

Zimmermann et al., "Hyphenation of Gas Chromatography and Resonance-Enhanced Laser Mass Spectrometry (REMPI-TOFMS): A Multidimensional Ananlytical Technique," J. High Resol Chromatography vol. 20 (9), 1997, pp. 461-470.

* cited by examiner

*Primary Examiner* — Hezron E Williams
*Assistant Examiner* — Gregory J Redmann
(74) *Attorney, Agent, or Firm* — Thomas F. Cooney

(57) ABSTRACT

A system for interfacing a gas chromatograph (GC) to a mass spectrometer the GC comprising a GC column partially contained within a GC oven, the mass spectrometer comprising a housing enclosing an interior having an ion source, the system comprising: a conduit extending from the GC oven to the mass spectrometer and comprising an interior volume that is contiguous with an interior volume of the GC oven; and a duct extending from a region of relatively high or relatively low pressure within the GC oven to the conduit interior volume and operable so as to transmit a flow of air or gas between the region of relatively high or relatively low pressure and the conduit interior volume, wherein a portion of the GC column extends through the conduit interior volume to the ion source.

15 Claims, 9 Drawing Sheets

`US 8,549,893 B2`

SYSTEM AND METHOD FOR A GAS CHROMATOGRAPH TO MASS SPECTROMETER INTERFACE

FIELD OF THE INVENTION

This invention relates to a mass spectrometer apparatus and in particular to a transfer system useful with a mass spectrometer and gas chromatograph.

BACKGROUND OF THE INVENTION

Mass spectrometers generally include an ion source disposed in a vacuum system for achieving analysis of chemical substances. In the powerful analytical technique known Gas Chromatography-Mass Spectrometry (GC-MS), volatile analytes from mixtures are first separated into individual components in a gas chromatograph (GC) and the separated samples are directly transferred into a mass spectrometer (MS) for subsequent mass analysis. The GC has a tubular column which is heated (or possibly cooled) to a controlled temperature or along a controlled temperature profile in a gas chromatograph oven (GC oven).

For clean separation of analytes, the temperature of a GC column needs to be carefully controlled, often to within a fraction of a degree. Further, in order to increase throughput, the temperature is often not maintained static during an entire separation, but is ramped along a controlled temperature profile. A GC oven for these purposes usually comprises a thermally insulated housing internally accessible through a door, a heating element, and a motor driven fan for stirring the air in the housing. The stirring fan continuously mixes the air within the oven to minimize temperature gradients which could adversely affect the performance of the chemical processes within the GC column. Various baffles or plenums are generally incorporated into the heated compartment of the GC oven in order to direct and control air flow. To facilitate rapid cooling or cool-down, a GC oven often typically comprises intake ports to allow air or gas to bleed into the oven and outlet ports to exhaust hot air or gas from the oven. For use with highly volatile compounds, the temperature of the GC oven may be accurately controlled at low temperatures (slightly above or even below ambient) by feeding air or a cooled gas into the inlet ports.

The effluent from the GC column needs to be transferred from the GC column, to the MS ion source that is held in vacuum. However, during the transfer (performed conventionally by means of a transfer line), it is necessary to maintain a uniform temperature across the length of the transfer line. If a significant temperature gradient exists so that the temperature varies at different points along the transfer line, cold spots may occur to cause condensation from the gas phase of the sample so that it will either not be passed through to the MS or will exhibit excessive chromatographic peak broadening or peak tailing. On the other hand, hot spots that appear may cause some compounds to degrade thermally with a resultant change in their chemical structure. Similar effects can occur even if the transfer line is at a uniform temperature if the temperature of the transfer line is either too cold or too hot during the elution of any given chemical compound. Additionally, excessive transfer line temperatures can lead to elevated "chemical noise" and lower signal-to-noise ratio for any given analytical results.

Prior art approaches for transferring column effluent to a mass spectrometer have employed isothermal, independently heated transfer lines comprising tubing situated between a gas chromatograph and a mass spectrometer and through which the GC column is passed. As one example, FIG. 1A illustrates a first conventional system for interfacing a gas chromatograph 10 to a mass spectrometer 20. The gas chromatograph 10 comprises a gas chromatograph oven having an insulated oven housing 19. The oven has a temperature controlled oven interior volume 18 containing at least a portion of GC column 12. The mass spectrometer 20 comprises housing 29 that has an interior 28 containing ion source 22. The mass spectrometer interior 28 is generally under vacuum during operation of the mass spectrometer. A portion of the GC column 12 passes through the full length of the interior of a transfer tube 14 and into the ion source 22. The GC column 12 is sealed to the transfer tube by vacuum fitting 13 and the transfer tube 14 is sealed to the mass spectrometer 20 by seal 16. As in other conventional systems for interfacing a gas chromatograph to a mass spectrometer, a portion of the GC column 12 resides within a section of the transfer tube 14 that is neither within the GC oven interior 18 nor the MS interior 28. The conventional system shown in FIG. 1A maintains this section at an appropriate temperature by means of a heating tape 11 wrapped around and in close thermal contact with the transfer tube 14. Resistance heating produced by electrical current supplied by electrical leads 15 elevates the temperature of the heating tape 11 and, consequently, of the sections of the transfer tube in contact with the heating tape and the GC column within the transfer tube.

FIG. 1B illustrates a second conventional system for interfacing a gas chromatograph 10 to a mass spectrometer 20. In the system shown in FIG. 1B, a separate box-like oven 17 that encloses a portion of the transfer tube is used instead of heating tape. Power is supplied to the oven 17 by electrical leads 15.

FIG. 1C illustrates a third conventional system for interfacing a gas chromatograph 10 to a mass spectrometer 20. The system shown in FIG. 1C comprises a transfer line 30 disposed between the gas chromatograph 10 and the mass spectrometer 20 that includes two additional tubes—a middle tube 32 and an outer tube 33—that enclose the transfer tube 14, which comprises an inner tube. The middle tube encloses, in addition to the transfer tube, a temperature sensor (not shown) and a heater (not shown) that extends along the full length of the middle tube adjacent to the inner tube. The space between the middle tube 32 and the outer tube 33 acts as insulation, thereby limiting heat transfer to the outer tube. This space may be under vacuum in order to provide thermal insulation, or may be packed with an insulative material such as glass or ceramic fibers.

These conventional approaches have experienced problems of either complexity, increased difficulty of accessing the GC column, non-uniformity of heat distribution within the transfer line, or non-matching of the transfer line temperature to the internal temperature of the GC oven. Although it would be possible to controllably ramp the interface temperature in accordance with the GC oven profile, the thermal mass of such devices precludes convenient and rapid cooldown to the initial conditions necessary for subsequent analysis. Further, using these conventional approaches, it is difficult to maintain a controlled temperature of the transfer line at near ambient conditions or at sub-ambient conditions.

SUMMARY OF THE INVENTION

In order to overcome the aforementioned problems associated with the conventional art, an improved gas chromatograph to mass spectrometer interface is herein disclosed. The gas chromatograph to mass spectrometer interface disclosed herein does not require any separate temperature controller for a transfer line but, instead, uses heated air directly from a GC oven blower to thermally regulate a GC column, possibly contained within a low thermal mass section of tubing.

Accordingly, various embodiments according to a first aspect of the invention may comprise a system for interfacing a gas chromatograph (GC) to a mass spectrometer, the GC comprising a GC column partially contained within a GC oven, the mass spectrometer comprising a housing enclosing an interior having an ion source, the system comprising: a conduit extending from the GC oven to the mass spectrometer and comprising an interior volume that is contiguous and conterminous with an interior volume of the GC oven; and a duct extending from the vicinity of a blower of the GC oven to the conduit interior volume and operable so as to transmit a flow of air or gas from the blower into the conduit interior volume, or to the blower from the conduit interior volume, wherein a portion of the GC column extends through the conduit interior volume to the ion source.

Various embodiments according to another aspect of the invention may comprise a method for interfacing a gas chromatograph (GC) to a mass spectrometer, wherein the GC comprises a GC column partially contained within a GC oven and the mass spectrometer comprises a housing enclosing an interior having an ion source, the method comprising: providing a conduit extending from the GC oven to the mass spectrometer and having an interior volume such that the conduit interior volume is contiguous and conterminous with an interior volume of the GC oven; providing a duct extending from the vicinity of a blower of the GC oven to the conduit interior volume so as to transmit a flow of air or gas to or from the blower into or out of the conduit interior volume; and routing a portion of the GC column through the conduit interior volume to the ion source.

Various embodiments according to still another aspect of the invention may comprise a method of operating a gas chromatograph-mass spectrometer (GC-MS) comprising a gas chromatograph column (GC column) for separating analytes of a sample, a gas chromatograph oven (GC oven) and a mass spectrometer, the method comprising: providing a conduit extending between the GC oven and the mass spectrometer such that an interior volume of the conduit is contiguous and conterminous with an interior volume of the GC oven; routing the GC column through the GC oven and through the conduit interior volume to an ion source of the mass spectrometer; providing a flow of air or gas to or from a blower of the gas chromatograph to the conduit interior volume; introducing the sample into the GC column; controlling the temperature of the interior volume of the GC oven and the interior volume of the conduit using the air or gas so as to facilitate analyte separation within the GC column and transfer of the separated analytes to the mass spectrometer; and analyzing the separated analytes with the mass spectrometer.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 2-3, taken in conjunction with the following description.

Figure 1A:
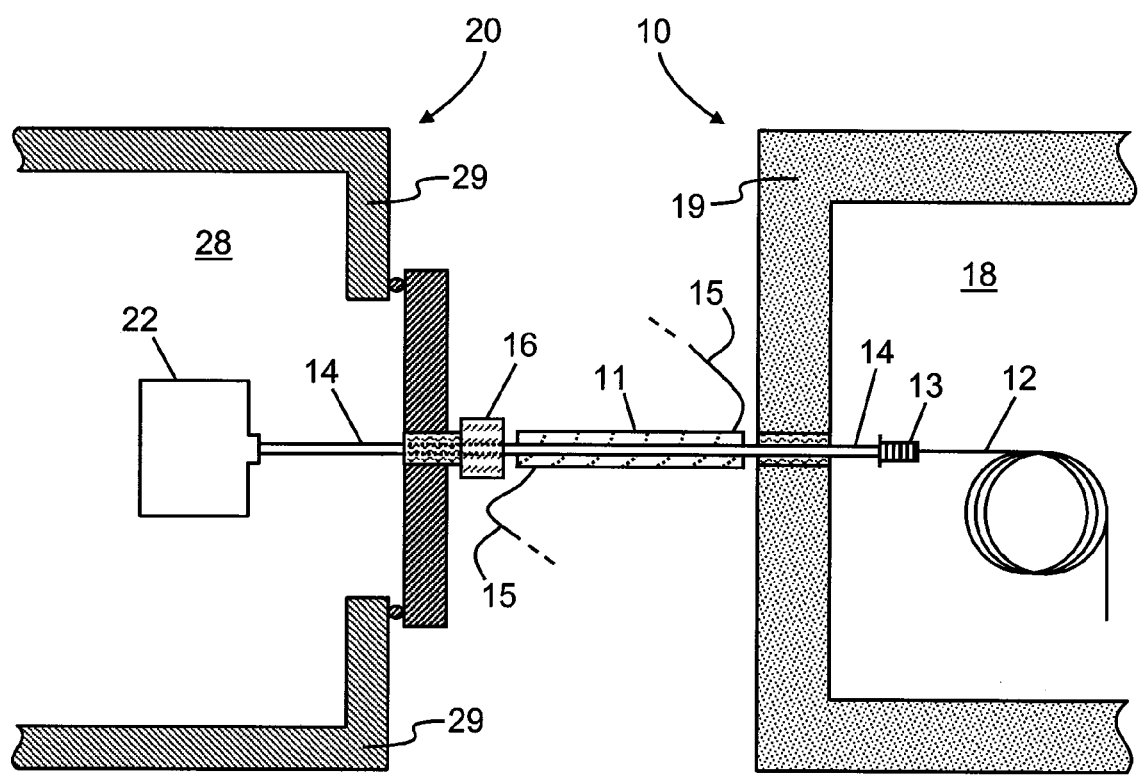
FIG. 1A is a schematic illustration of a first conventional system for interfacing a gas chromatograph to mass spectrometer.
Figure 1B:
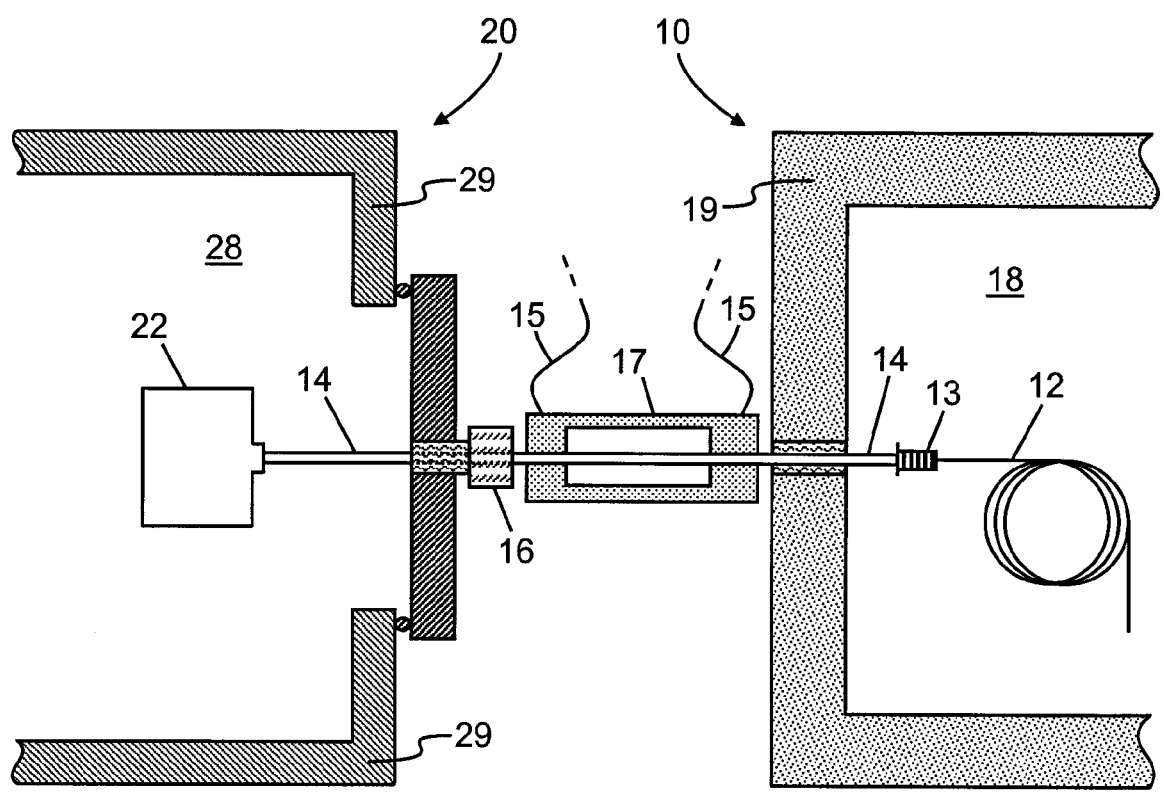
FIG. 1B is a schematic illustration of a second conventional system for interfacing a gas chromatograph to mass spectrometer.
Figure 1C:
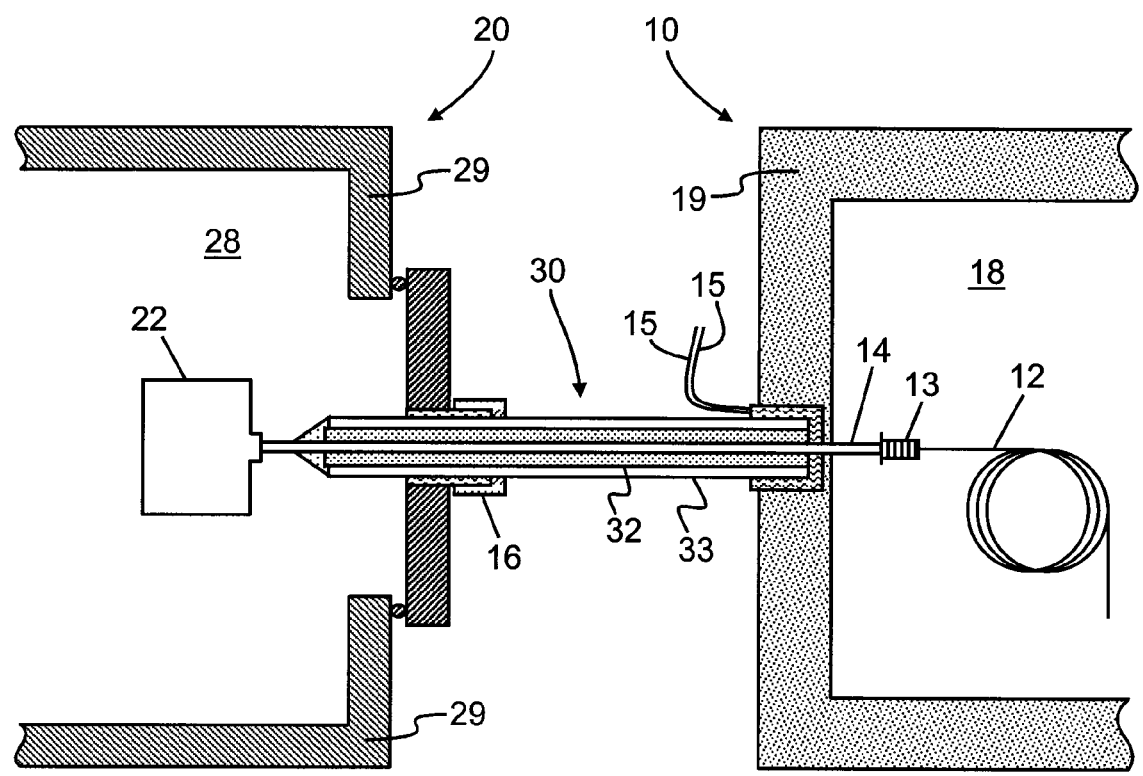
FIG. 1C is a schematic illustration of a third conventional system for interfacing a gas chromatograph to mass spectrometer.
Figure 2A:
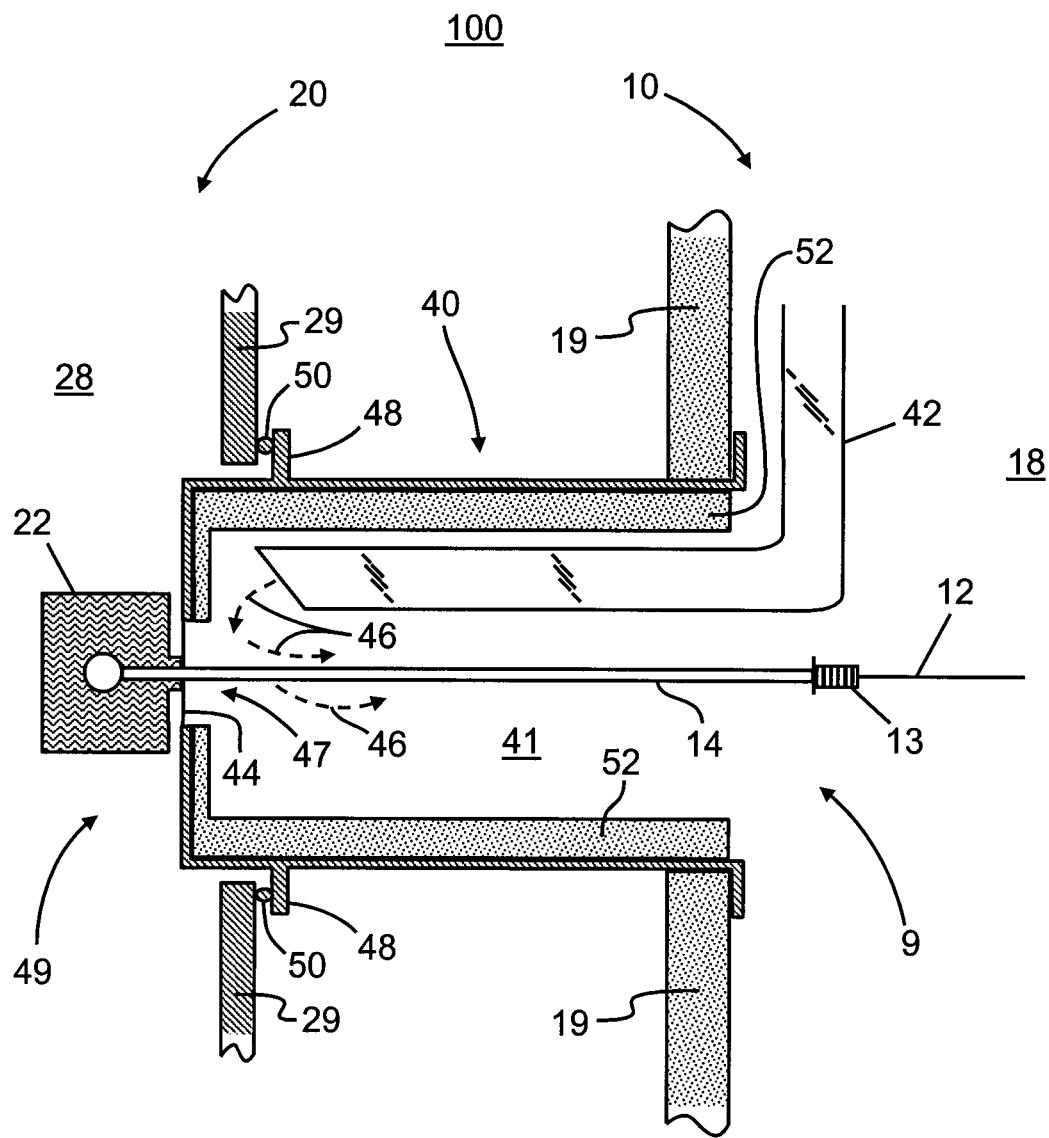
FIG. 2A is a schematic illustration of a first gas chromatograph to mass spectrometer interface in accordance with some embodiments of the present invention.

FIG. 2A is a schematic illustration of a gas chromatograph to mass spectrometer interface in accordance with the present invention. In FIG. 2A, reference number 10 refers to a gas chromatograph (only a portion of which is illustrated) and reference number 20 refers to a mass spectrometer (only a portion of which is illustrated). The system 100 shown in FIG. 2A comprises a conduit 40 which partially encloses an interior volume 41 which is contiguous and conterminous with the heated GC oven interior volume 18. The conduit 40 is sealed, in an air-tight fashion, to the housing 19 of the GC oven and extends outward from the housing 19 and between the GC and the MS such that the conduit interior volume 41 comprises an outward extension of the interior volume 18 of the GC oven. This configuration enables the heated internal air or gas of the oven to flow into or out of the conduit interior volume 41. The conduit 40 is preferably lined with a low thermal mass rigidized ceramic fiber insulation 52 in order to minimize thermal lag and heat loss to the outer shell of the conduit 40. The use of rigidized insulation allows operation without heat loss to a metallic liner (such as is typically used in the lining of a GC oven) while at the same time prevents erosion of the insulator as would occur for loose glass or ceramic wool type insulation materials. As one example, the insulation 52 may comprise the material HTP as is described in NASA Tech Briefs, Winter 1985, Vol. 4, MSC-20654.

A duct 42 in the system 100 (FIG. 2A) channels higher pressure oven-heated air from periphery of an oven blower or fan into the conduit interior volume 41 such that flowing temperature regulated air or gas 46 flows along and around the entire length of the transfer tube 14 contained within the volume 41. This free flow of air around and along the transfer tube 14 allows thermal regulation of the section of the GC column contained within the transfer tube within the conduit interior volume. Preferably, the end of the duct disposed within the conduit should be placed such that the flowing temperature-regulated air or gas arrives or exits at or close to the end of the conduit 40 furthest from the GC oven. This ensures that no dead volume remains in the conduit which would otherwise result in a temperature gradient along its length.

The transfer tube 14 should be sufficiently rigid to support the column but should have sufficiently low thermal mass so as to enable oven temperature changes to be communicated to the section of column within the transfer tube with suitably low time lag. This enables the temperature of the column within volume 41 to track the controlled temperature of the oven interior 18 without resulting in adverse band broadening, peak tailing or sample decomposition. As one example, the inventors have discovered that 1.6 millimeter (mm) or 1/16 inch or smaller outer diameter stainless steel tubing fulfills these requirements. However, the tubing may have a larger diameter (up to 2 mm) in order to accommodate the largest available diameter capillary GC column. The transfer tube 14 is preferably terminated in the GC oven proper in order to conveniently access vacuum fitting 13 for column installation and removal. Although the vacuum fitting 13 could be positioned closely to ion source 22 in order to further reduce thermal mass, thus tracking overall oven temperature more accurately, it is preferable that some degree of thermal mass near the terminal end of the GC column is present in order to offset potential peak splitting due to the laminar air flow conditions in this area. The effects of peak splitting caused by rapid GC temperature fluctuations are described in F. Munari and S. Trestianu "Thermal peak splitting in capillary gas chromatography" Journal of Chromatography, 279 (1983) 457-472.

The system shown in FIG. 2A extends accurate heating control of the column to within close proximity to the mass spectrometer 20. As seen in the example of FIG. 2A, the end of the conduit 40 may protrude past or beyond the mass spectrometer housing 29 through a gap or aperture 49 in the MS housing 29. The vacuum within the mass spectrometer may be sealed against ambient air intrusion by means, for instance, of a flange 48 that is sealed, in vacuum-tight fashion by means of a gasket or O-ring 50, against a wall or other structural feature of the MS housing.

Air or gas from within the GC oven is prevented from entering the mass spectrometer and the integrity of the MS vacuum may be maintained (while maintaining proximity of the conduit interior volume 41 to the mass spectrometer 20) by means of a membrane 44 through which the column-containing transfer tube passes and which comprises an air-tight and vacuum tight seal over exit port 47 of the conduit 40. As one example, the membrane may comprise a stainless steel foil of thickness within the range of approximately 0.010 to 0.020 inches. The diameter and thickness of the membrane 44 can be selected so as to offer minimal heat loss from oven air to the structural enclosure of conduit 40, while at the same time offering sufficient strength to avoid a vacuum rupture imposed by the high vacuum of the MS interior 28. Additionally, this membrane allows sufficient heating of terminal end of transfer tube 14 by ion source 22 without excessive heat loss from the ion source.

The conduit 40 may comprise an integral part of the GC oven housing 19. Alternatively, the conduit 40 may be provided as a modular accessory that attaches to or mates with a pre-existing gap 9 in a wall of the GC oven. For instance, the gap 9 may comprise a pre-existing output port or aperture, such as, for instance, a port or aperture to which various accessory apparatuses (e.g., detectors) may be interchangeably mated or fitted.

Figure 2B:
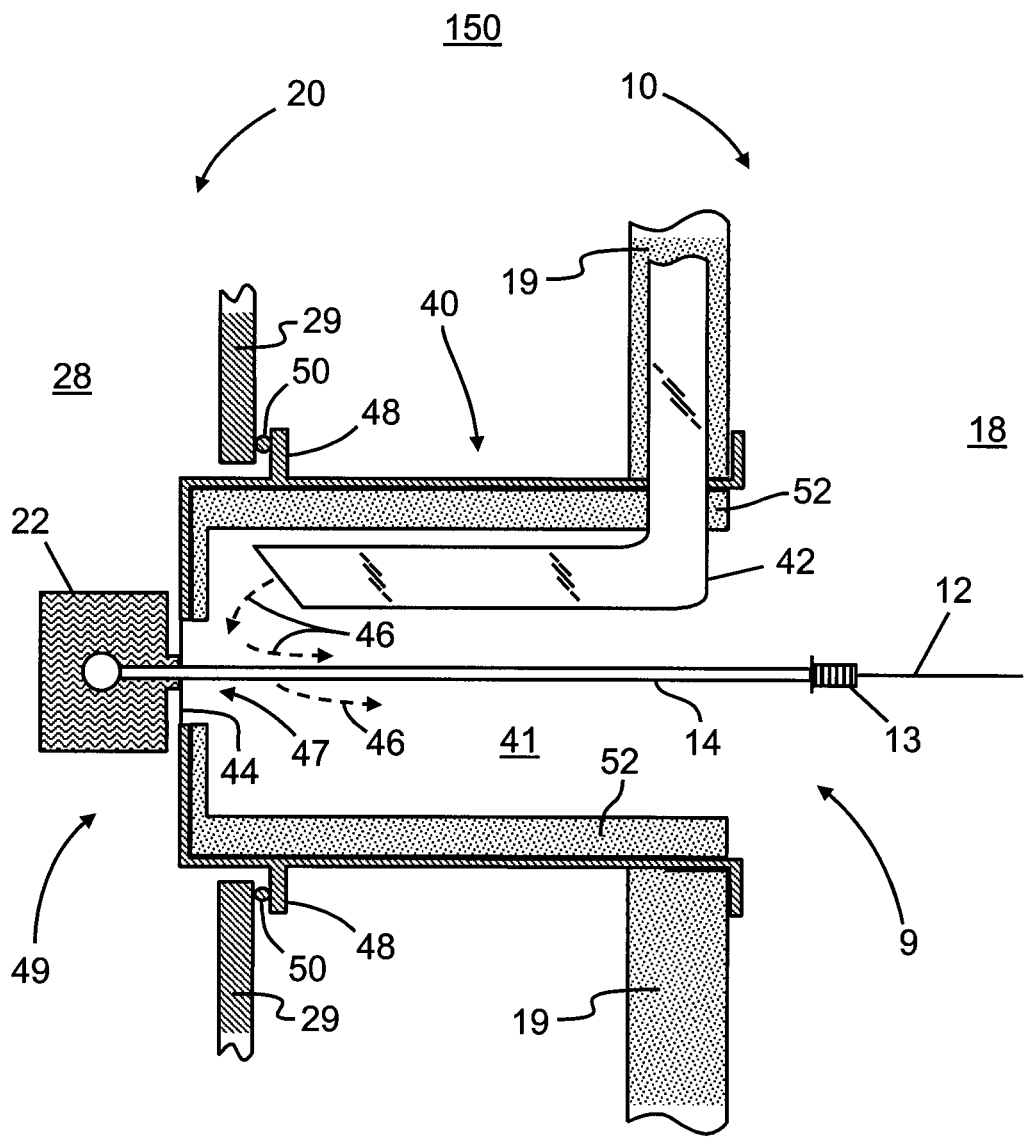
FIG. 2B is a schematic illustration of a second gas chromatograph to mass spectrometer interface in accordance with some embodiments of the present invention.

FIG. 2B illustrates an embodiment, in accordance with the invention, in which a portion of the duct 42 is located within a portion (such as a wall portion) of the GC oven housing 19. This configuration frees up space within the interior of the GC oven for positioning a portion of the column. Further, the configuration shown in FIG. 2B may cause less interruption of the air or gas flow within the GC oven.

Figure 3A:
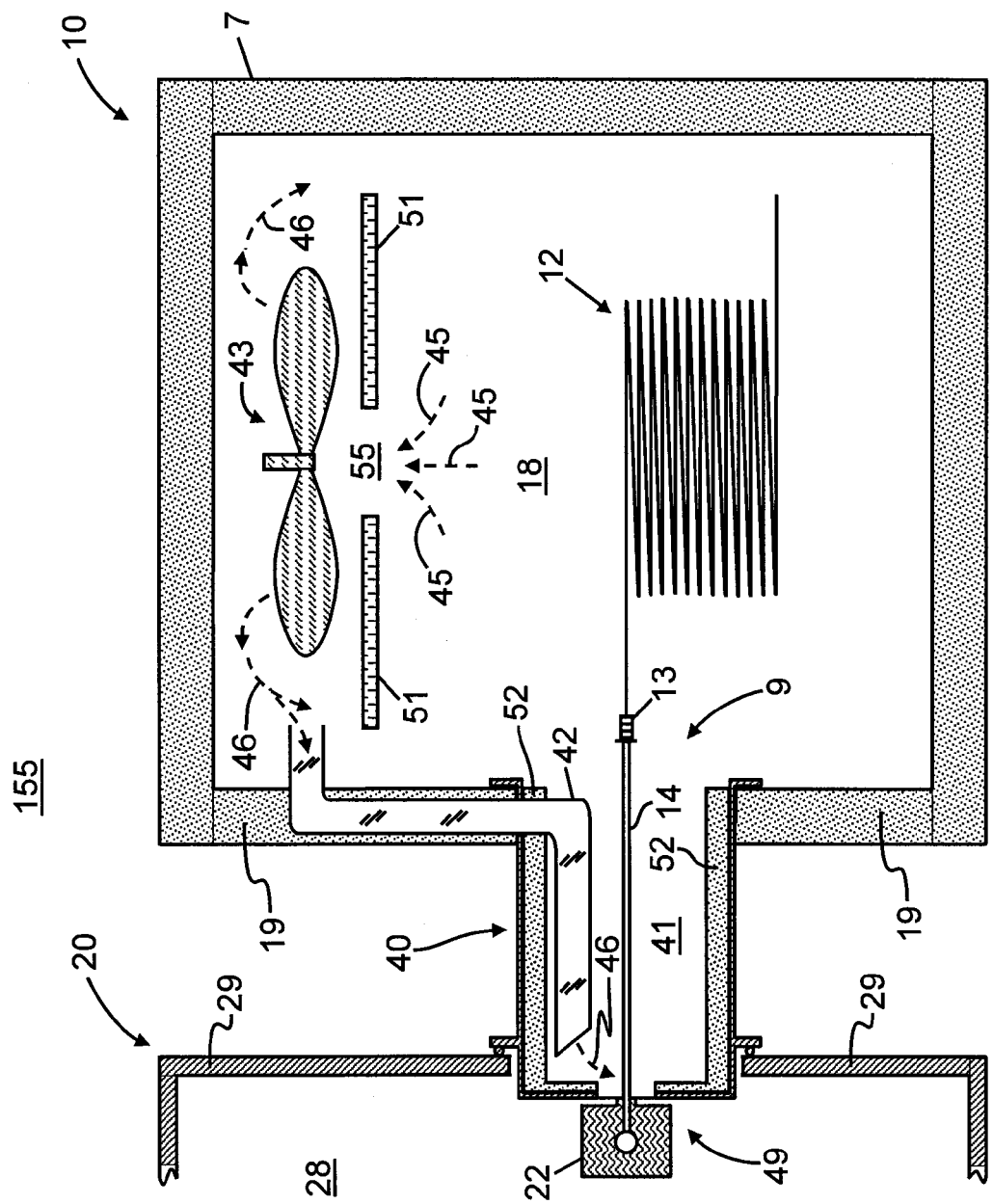
FIG. 3A is a schematic illustration of a gas chromatograph to mass spectrometer interface partially contained within a GC oven in accordance with some embodiments of the present invention.

FIG. 3A is a schematic illustration of a gas chromatograph to mass spectrometer interface 155 partially contained within a GC oven 7 and showing one method of fluidic coupling between an inlet of the duct 42 and a fan or blower 43 within the GC oven 7. As shown in FIG. 3A, the inlet of the duct 42 may be disposed behind a plenum or partition 51 within the GC oven so as to intercept the radial flow of flowing gas 46 emanating from the blower fan 43. Returning air or gas 45 is drawn in towards fan 43 and is channeled towards the central hub of the fan 43 by one or more gaps 55 of or within the plenum or partition 51. The gaps 55 may comprise, for instance, perforations or slits within the plenum or partition 51. In the configuration shown in FIG. 3A, air or gas set in motion by fan 43 is forced to flow laterally outward in a region between the plenum 51 and the GC oven housing 19 as a result of confinement between these latter two elements. Consequently, a pressure differential is established with a relatively higher pressure region existing laterally outward from the fan 43 between the plenum 51 and the GC oven housing 19. As shown in FIG. 3A, the inlet of the duct 42 is disposed so as to intercept a portion of the air or gas within this high pressure region and direct it into the relatively lower pressure conduit interior volume 41. FIG. 3A illustrates an embodiment in which a portion of the duct 42 is contained within the GC oven housing 19 as shown in FIG. 2B. However, the configuration illustrated in FIG. 2A, configuration in which the duct is positioned within the GC oven interior, could also be used.

Figure 3B:
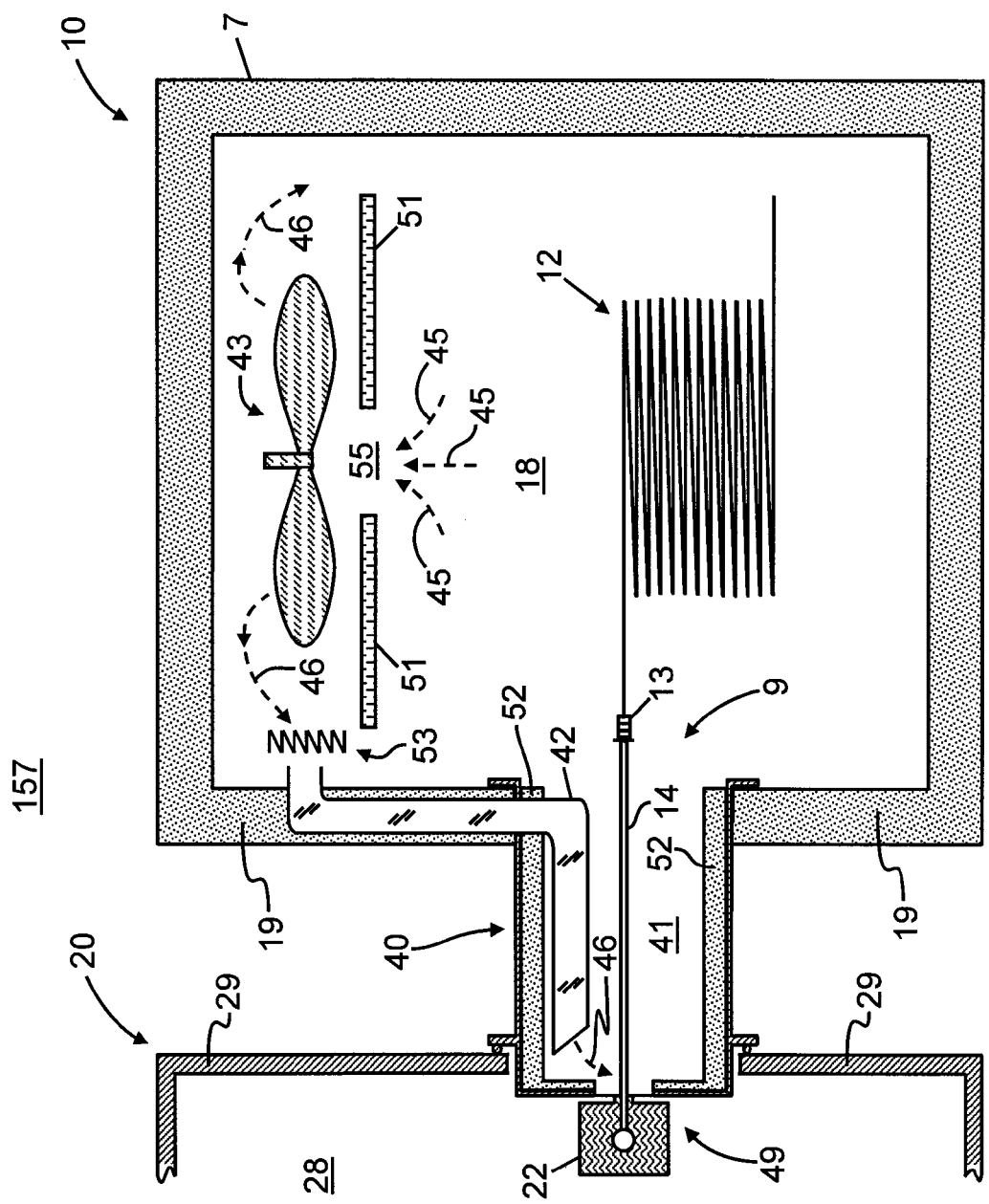
FIG. 3B is a schematic illustration of another gas chromatograph to mass spectrometer interface partially contained within a GC oven in accordance with some embodiments of the present invention.

FIG. 3B is a schematic illustration of another gas chromatograph to mass spectrometer interface 157 partially contained within a GC oven 7. The system 157 shown in FIG. 3B is similar to the system 155 shown in FIG. 3A, except that, in the system 157, a heater or heating element 53 is positioned between the fan or blower 43 and the inlet of the duct 42. In this configuration, air or gas 46 is forced to flow adjacent to the heater 53 just prior to entering the duct 42. This configuration can compensate for any heat losses along the length of the duct. Although FIG. 3B illustrates a configuration in which a portion of the duct 42 is contained within the GC oven housing 19 (i.e., as in FIG. 2B), the configuration in which the duct is positioned within the GC oven interior (i.e., as in FIG. 2A) could also be used.

Figure 3C:
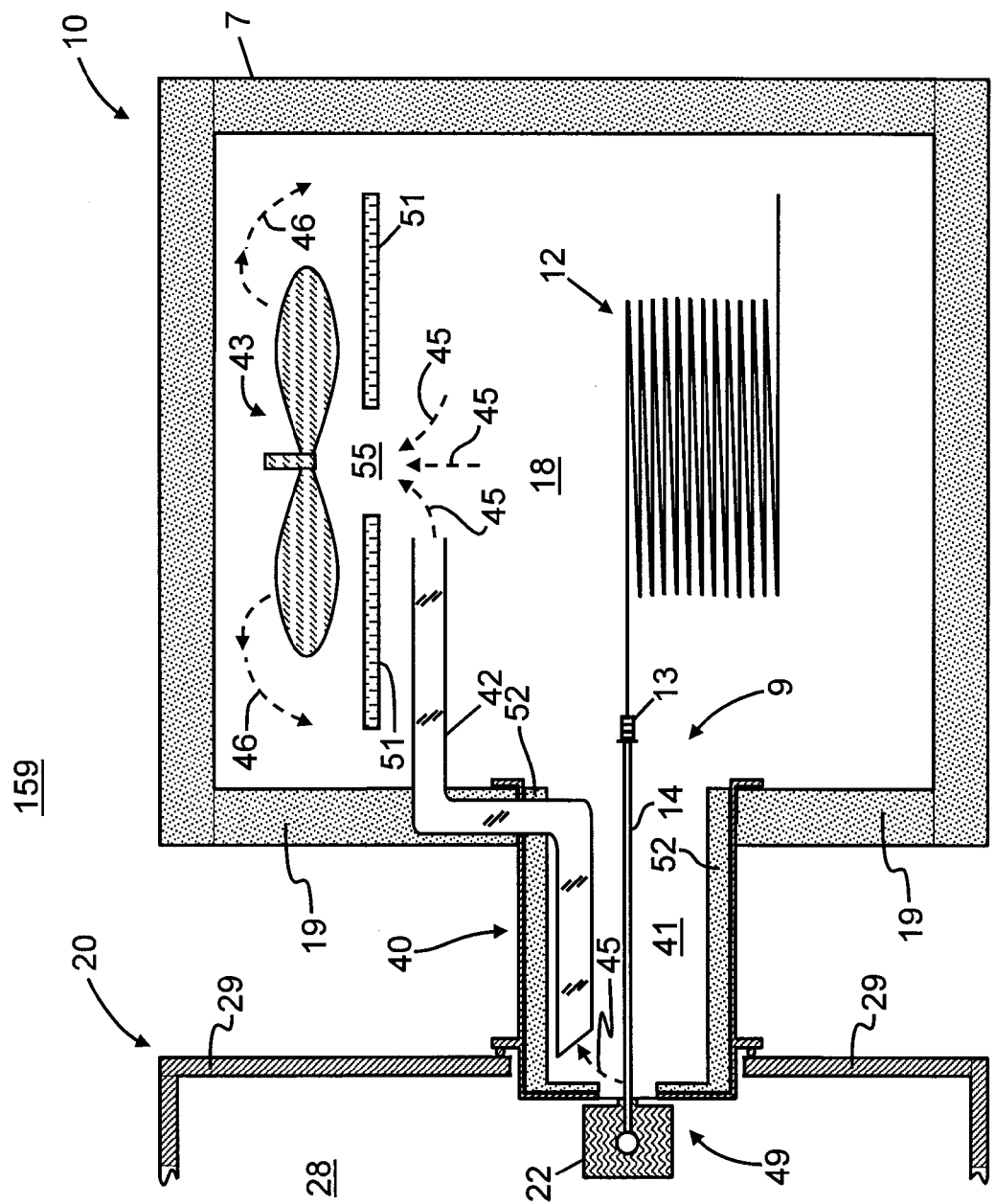
FIG. 3C is a schematic illustration of still another gas chromatograph to mass spectrometer interface partially contained within a GC oven in accordance with some embodiments of the present invention.

FIG. 3C is a schematic illustration of still another gas chromatograph to mass spectrometer interface 159 partially contained within a GC oven 7 and showing another method of fluidic coupling between an inlet of the duct 42 and the fan or blower 43. In the configuration shown in FIG. 3C, the inlet of the duct 42 is positioned within a relatively lower pressure region near the gap (or gaps) 55 in the plenum or partition 51. In this situation, the duct draws returning air or gas 45 out of the conduit interior volume 41, causing temperature regulated air or gas to flow from the GC oven interior 18 into the conduit interior volume 41. Alternatively, any location within the GC oven confines offering a pressure differential is suitable in order to establish flow within the duct 42. Although FIG. 3C illustrates a configuration in which a portion of the duct 42 is contained within the GC oven housing 19 (i.e., as in FIG. 2B), the configuration in which the duct is positioned within the GC oven interior (i.e., as in FIG. 2A) could also be used.

Figure 3D:
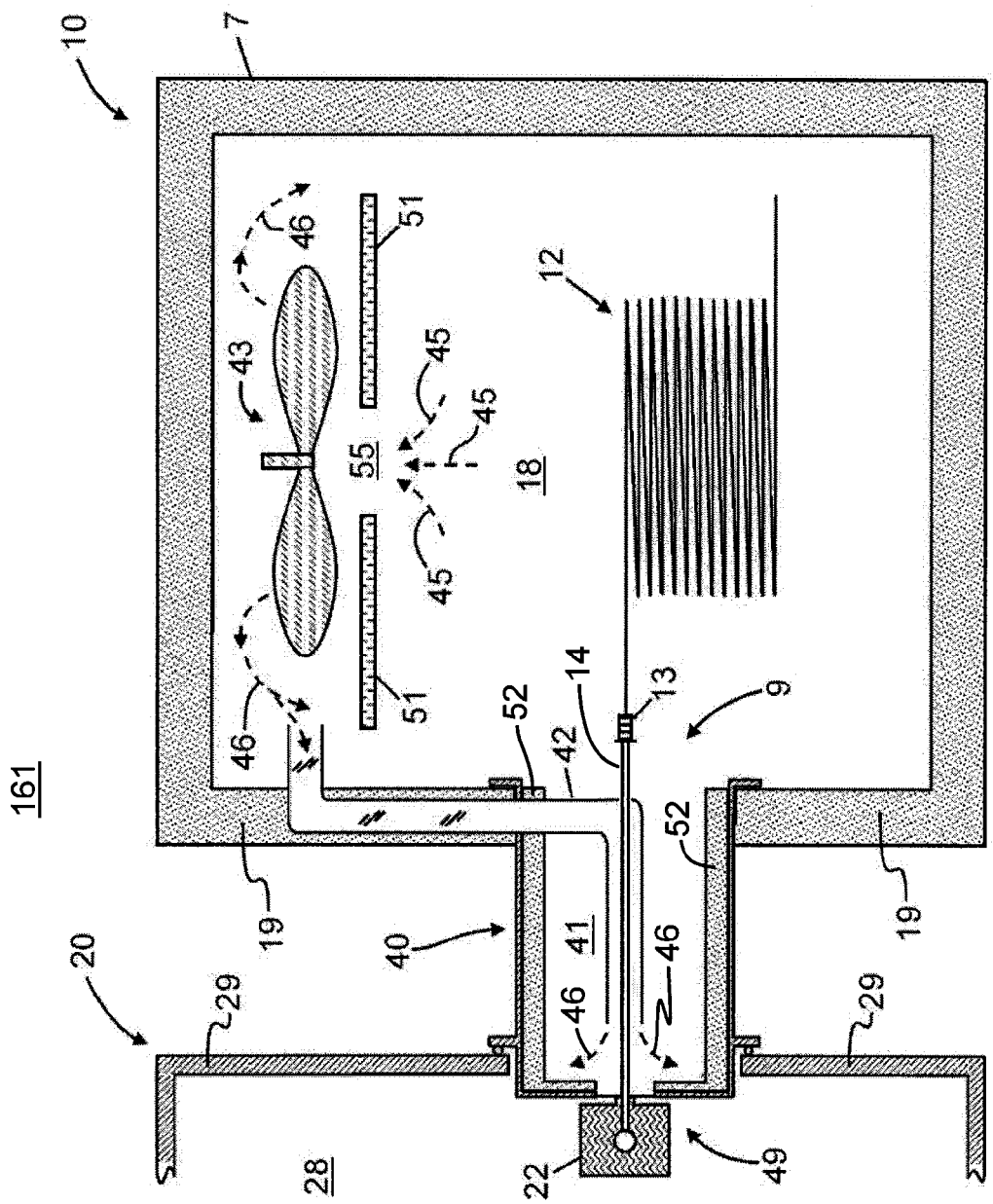
FIG. 3D is a schematic illustration of yet another gas chromatograph to mass spectrometer interface partially contained within a GC oven in accordance with some embodiments of the present invention.

FIG. 3D illustrates is a schematic illustration of yet another gas chromatograph to mass spectrometer interface 161 partially contained within a GC oven 7. In the configuration illustrated in FIG. 3D, a portion of the duct 42 within the conduit 40 encloses a portion of the transfer tube 14 such that the flowing temperature regulated air or gas 46 is confined along the portion of the transfer tube 14, thereby improving heat transfer from the air or gas 46 to the transfer tube. Although FIG. 3D illustrates a configuration in which a portion of the duct 42 is contained within the GC oven housing 19 (i.e., as in FIG. 2B), the configuration in which the duct is positioned within the GC oven interior (i.e., as in FIG. 2A) could also be used.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. Neither the description nor the terminology is intended to limit the scope of the invention. Any publications, patents or patent application publications mentioned in this specification are explicitly incorporated by reference in their respective entirety.

What is claimed is:

1. A system for interfacing a gas chromatograph (GC) to a mass spectrometer, the GC comprising a GC column partially contained within an interior volume of a GC oven, the mass spectrometer comprising a housing enclosing an interior having an ion source, the system comprising:
    a conduit extending from the GC oven to the mass spectrometer and comprising a conduit interior volume that is contiguous with the interior volume of the GC oven and fluidically coupled thereto such that a portion of the GC column extends through the conduit interior volume to the ion source;
    a tubular duct having a first end within the GC oven interior volume and a second end within the conduit interior volume, a portion of a length of which is within the conduit interior volume; and,
    a blower or fan within the interior volume of the GC oven and operable to generate an air or gas flow circulation comprising a first circulation portion outside of and directed away from the GC oven interior volume and a second returning circulation portion outside of and directed towards the GC oven interior volume,
    wherein the conduit, the duct and the blower or fan are configured such that, in operation, one of the first and second circulation portions is within the duct and the other one of the circulation portions is within the conduit.

2. The system of claim 1, further comprising a transfer tube containing the portion of the GC column that extends through the conduit interior volume.

3. The system of claim 2 wherein a portion of the duct encloses at least a portion of the transfer tube.

4. The system of claim 2, wherein the transfer tube comprises stainless steel tubing of less than or equal to 2 millimeters diameter.

5. The system of claim 2, wherein the conduit protrudes through a gap in the mass spectrometer housing.

6. The system of claim 5, further comprising a non-permeable membrane through which the transfer tube passes, the membrane separating the mass spectrometer interior from the conduit interior volume, the GC column passing through the membrane.

7. The system of claim 6, wherein the membrane comprises stainless steel foil having a thickness within the range of 0.010-0.020 inches.

8. The system of claim 1, wherein the conduit is lined with a thermal insulation comprising low thermal mass rigidized ceramic fiber.

9. A method for interfacing a gas chromatograph (GC) to a mass spectrometer, wherein the GC comprises a GC column partially contained within an interior volume of a GC oven and wherein the mass spectrometer comprises a housing enclosing an interior having an ion source, the method comprising:
    providing a conduit having a conduit interior volume so as to extend from the GC oven to the mass spectrometer such that the conduit interior volume is contiguous with and fluidically coupled to the interior volume of the GC oven;
    providing a tubular duct having a first end, a second end and a length such that a portion of the length of the tubular duct is within the conduit interior volume;
    routing a portion of the GC column through the conduit interior volume to the ion source; and
    providing a blower or fan within the interior volume of the GC oven,
    wherein the conduit, the duct and the blower or fan are provided such that, in operation, the blower or fan generates an air or as flow circulation comprising a first circulation portion outside of and directed away from the GC oven interior volume and a second returning circulation portion outside of and directed towards the GC oven interior volume such that one of the first and second circulation portions is within the duct and the other one of the circulation portions is within the conduit.

10. The method of claim 9, further comprising:
    providing a transfer tube so as to contain the portion of the GC column within the conduit interior volume.

11. The method of claim 9, wherein the step of providing a conduit so as to extend from the GC oven to the mass spectrometer includes situating the conduit such that a portion of the conduit protrudes through a gap in the mass spectrometer housing.

12. The method of claim 9, further comprising:
    providing a non-permeable membrane separating the mass spectrometer interior from the conduit interior volume such that the GC column passes through the membrane.

13. The method of claim 12 further comprising:
    providing a transfer tube so as to contain the portion of the GC column within the conduit interior volume and so as to pass through the membrane.

14. The method of claim 9, wherein the first circulation portion is within the duct.

15. The method of claim 9, wherein the second circulation portion is within the duct.

\* \* \* \* \*